(12) United States Patent
Poulsen

(10) Patent No.: US 10,545,126 B2
(45) Date of Patent: Jan. 28, 2020

(54) ARTICLES AND METHODS FOR SENSORY TRAINING, EDUCATION, ENTERTAINMENT, OR AMUSEMENT

(71) Applicant: Peter D. Poulsen, Grants Pass, OR (US)

(72) Inventor: Peter D. Poulsen, Grants Pass, OR (US)

(*) Notice: Subject to any disclaimer, the term of this patent is extended or adjusted under 35 U.S.C. 154(b) by 986 days.

(21) Appl. No.: 15/004,885

(22) Filed: Jan. 22, 2016

(65) Prior Publication Data
US 2017/0212089 A1    Jul. 27, 2017

(51) Int. Cl.
G09B 25/00    (2006.01)
G01N 33/00    (2006.01)
G09B 5/00    (2006.01)
G09B 1/32    (2006.01)

(52) U.S. Cl.
CPC ........... *G01N 33/0001* (2013.01); *G09B 1/32* (2013.01); *G09B 5/00* (2013.01)

(58) Field of Classification Search
USPC .............. 434/247, 258, 365, 367, 370, 433; 273/459; 446/71, 75, 227, 267, 491
See application file for complete search history.

(56) References Cited

U.S. PATENT DOCUMENTS

| | | | | |
|---|---|---|---|---|
| 3,484,105 A | * | 12/1969 | Winston ................. | A63F 9/0098 273/440 |
| 4,772,240 A | * | 9/1988 | Boskovic ................ | A63F 7/042 273/109 |
| 6,053,738 A | * | 4/2000 | Ivey, Jr. .................. | A61L 9/125 273/460 |
| 6,419,497 B1 | * | 7/2002 | Carlson ................ | G09B 21/003 217/11 |
| D539,848 S | * | 4/2007 | Boutin .......................... | D19/59 |
| 8,672,680 B2 | * | 3/2014 | Baklanov .................. | G09F 3/02 273/DIG. 24 |
| 2002/0006763 A1 | * | 1/2002 | Forbes .................. | A63F 9/0666 446/1 |
| 2002/0009695 A1 | * | 1/2002 | Rasheed ................ | G09B 11/00 434/85 |
| 2005/0073105 A1 | * | 4/2005 | Given .................... | A63B 67/00 273/449 |
| 2010/0227525 A1 | * | 9/2010 | Smith .................... | A63H 33/38 446/149 |
| 2011/0311953 A1 | * | 12/2011 | Goll ........................ | G09B 1/00 434/191 |

* cited by examiner

*Primary Examiner* — Kurt Fernstrom
(74) *Attorney, Agent, or Firm* — David S. Alavi

(57) ABSTRACT

An object is enclosed but moveable within a container. An interior surface of the container includes two or more distinct areal segments exhibiting corresponding surface characteristics. Movement of the object while in contact with each areal segment results in a corresponding sensory input to a user moving the container. The corresponding surface characteristic of each areal segment differs from the corresponding surface characteristic of at least one other areal segment, so that the corresponding sensory inputs to the user resulting from movement of the object while in contact with those areal segments differ from one another. The corresponding sensory inputs can include auditory inputs, tactile inputs, visual inputs, olfactory inputs, or sensor readouts. The article can be employed in methods wherein a user identifies the object, or characterizes the object or areal segments, based on the sensory inputs.

24 Claims, 5 Drawing Sheets

US 10,545,126 B2

ARTICLES AND METHODS FOR SENSORY TRAINING, EDUCATION, ENTERTAINMENT, OR AMUSEMENT

FIELD OF THE INVENTION

The field of the present invention relates to toys, puzzles, and similar articles used for training, education, entertainment, or amusement purposes.

SUMMARY

An article comprises a container and an object enclosed within the container; often a single solid object is enclosed within the container. An interior volume of the container is at least partly bounded by an interior surface of the container that includes two or more distinct areal segments; each one of the areal segments exhibits a corresponding surface characteristic. The one or more objects are at least partly constrained to remain within the interior volume of the container and are movable within the interior volume of the container. Movement of each one of the one or more objects while in contact with each one of the areal segments results in a corresponding sensory input to a user moving the container. The corresponding surface characteristic of each one of the areal segments differs from the corresponding surface characteristic of at least one other of the areal segments. As a result, the corresponding sensory input to the user resulting from movement of a given one of the one or more objects while in contact with that areal segment differs from the corresponding sensory input resulting from movement of the given object while in contact with at least one other of the areal segments. The corresponding sensory inputs can include auditory inputs or tactile inputs, and can also include visual inputs or olfactory inputs or sensor readouts.

A user can be given the container with the one or more objects enclosed within the container and asked to identify one or more of the objects without opening the container, or to infer or deduce characteristics of one or more of the objects or areal segments without opening the container. That sequence can be repeated with the same one or more objects enclosed within in a different container, a different or additional one or more objects enclosed within the same container, or a different or additional one or more objects enclosed within a different container. The user's performance can be quantified or evaluated. The user can be told either the identity of one or more of the objects or the characteristics of one or more of the areal segments beforehand. Instead of one or more objects enclosed within a container, a portable computing device that includes one or more spatial sensors and one or more sensory output mechanisms can be employed to simulate the sensory experience a user would perceive when moving the container with the one or more objects enclosed within the container.

Objects and advantages pertaining to toys, puzzles, and similar articles used for training, education, entertainment, or amusement purposes may become apparent upon referring to the example embodiments illustrated in the drawings and disclosed in the following written description or appended claims.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

The embodiments depicted are shown only schematically: all features may not be shown in full detail or in proper proportion, certain features or structures may be exaggerated relative to others for clarity, and the drawings should not be regarded as being to scale. The embodiments shown are only examples: they should not be construed as limiting the scope of the present disclosure or appended claims.

DETAILED DESCRIPTION OF EMBODIMENTS

The articles and methods disclosed herein can be employed for a variety of purposes, including entertainment, amusement, education, or training purposes. Entertainment or amusement purposes can include use (individually, collaboratively, or competitively) as a toy or as a game (e.g., purchased or as a giveaway or promotion, given or received as a gift, given or received as a prize, and so forth). Education or training purposes can include various teaching, diagnostic, evaluative, or therapeutic purposes, e.g., physical, occupational, behavioral, or rehabilitative therapies employed to treat individuals, e.g., that are recovering from a stroke or other brain injury, other trauma or illness, or have a congenital or developmental abnormality or deficit. The disclosed articles and methods exploit natural human curiosity about one's surroundings. For example, when handed a wrapped package, a person's first instinct is to shake the box in an attempt to identify the contents based on weight, feel, and sound.

Figures 21, 22:
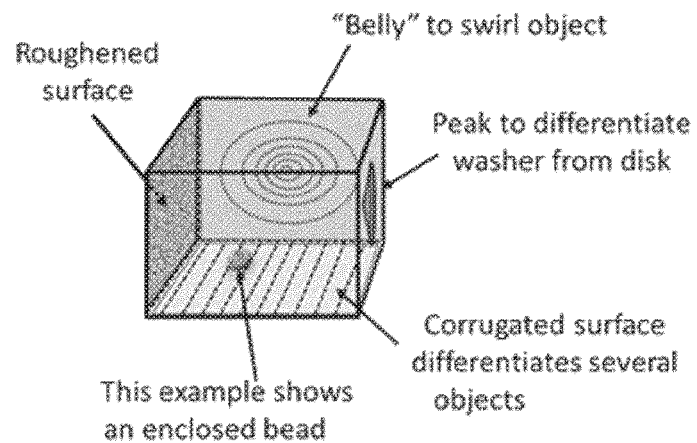
FIG. 21 illustrates an example of a container with multiple areal regions having different surface characteristics interacting with an object enclosed within the box.
FIG. 22 illustrates an example of a score sheet for recording observed sensory inputs from an object within a container.

An article according to the present disclosure comprises a container and one or more objects enclosed within the container; often a single solid object is enclosed within the container (e.g., as in FIG. 21). Subsequent descriptions herein of a single enclosed object shall be construed as also encompassing instances in which multiple objects are enclosed within the container. An interior volume of the container is at least partly bounded by an interior surface of the container that includes multiple distinct areal segments; each one of the areal segments exhibits a corresponding surface characteristic. The object is at least partly constrained to remain within the interior volume of the container and is movable (freely or perhaps further constrained in some manner) within the interior volume of the container. Movement of the object while in contact with each one of the areal segments results in a corresponding sensory input to a user holding the container. In many examples the interior volume of the container is entirely bounded by the interior surface of the container so that the object is constrained to remain within the interior volume of the container.

Figure 7:
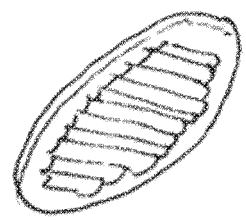
FIG. 7 illustrates schematically a corrugated cup lid.
Figure 8:
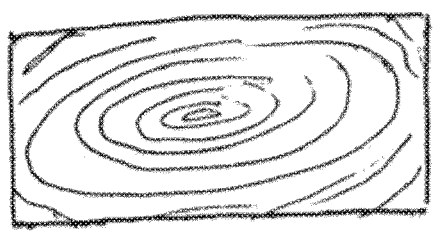
FIG. 8 illustrates schematically a flat, textured surface.
Figure 9:
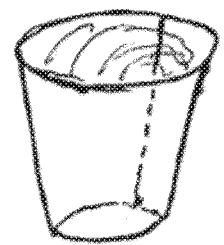
FIG. 9 shows that surface rolled into a frusto-conical shape.
Figure 10:
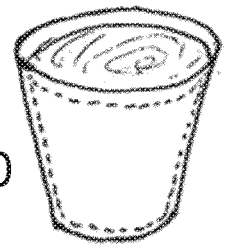
FIG. 10 shows that rolled surface inserted into a drinking cup.
Figure 12:
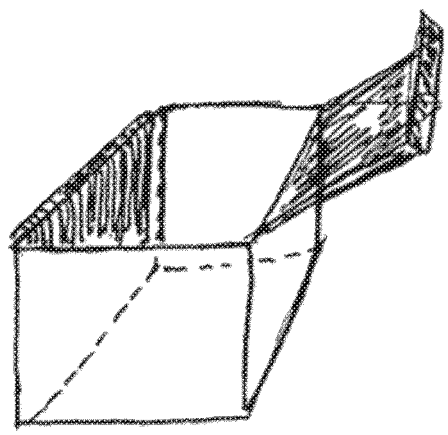
FIG. 12 show that surface mounted within a box.
Figure 11:
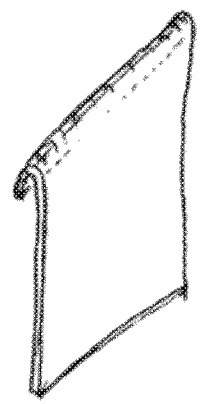
FIG. 11 illustrates schematically an interchangeable textured surface with a hooked top edge for engaging a box.
Figure 13:
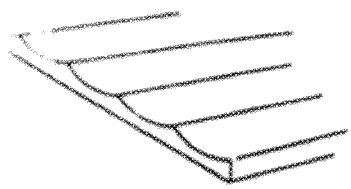
FIG. 13 illustrates schematically a corrugated surface.

The container can be shaped as any one of myriad three-dimensional shapes, including but not limited to being shaped as a sphere, spheroid, ellipsoid, or ovoid, as a circular or elliptical or oval cylinder or disk, as a circular or elliptical or oval annulus, as a torus or toroid or toroidal polyhedron, as a cube or cuboid, as a rhombohedron or parallelepiped, as a polygonal prism, as a circular or elliptical cone or frustum (i.e., a truncated cone, as in FIG. 10), as a polygonal pyramid or frustum (i.e., a truncated pyramid), or as a polyhedron. A common, almost archetypal example is a cube or cuboid, i.e., an ordinary, six-sided rectangular box (FIGS. 12 and 21). The container can be constructed from any one or more suitable materials, including but not limited to metal, wood, paper or cardboard, plastic, elastomer, composite, and so forth. In some examples the distinct areal segments can coincide with natural divisions of the surface shape of the container (e.g., each flat face of a cube can be one of the distinct areal segments as in the example of FIG. 21, or the ends and side surface of a cylindrical container can each be one of the distinct areal segments). That need not be the case, however, and the distinct areal segments can be arranged around the interior surface of the container in any suitable, desirable, or necessary way. In some examples, a purpose-made container can be employed; on other examples, a repurposed container can be employed, such as a shipping box, meal container, or a drinking cup (FIG. 10) with a lid (FIG. 7). Various inserts, lids, covers, or other components can be employed with a repurposed container, e.g., different interchangeable flat panels can be inserted into a used shipping box or meal container (FIGS. 11 and 12), a textured lid can be provided with a drinking cup (FIG. 7), or a textured thermal sleeve can be inserted into the cup (FIG. 8-10), e.g., after the drink is consumed. The preceding examples are not intended to constitute an exhaustive list; additional suitable shapes and arrangements of the container and its areal segments shall fall within the scope of the present disclosure or appended claims.

The corresponding surface characteristic of each one of the areal segments differs from the corresponding surface characteristic of at least one other of the areal segments. Some examples: each of the six sides of a cuboidal container can exhibit one of six distinct surface characteristics, or opposing pairs of sides can each exhibit one of three distinct surface characteristics, or the top and bottom can exhibit one surface characteristic while the four sides exhibit another, and so on; the ends of a cylindrical container can exhibit two different surface characteristics while the side surface exhibits a third, or the side surface can be divided transversely into rings exhibiting different surface characteristics, or the side surface can be divided lengthwise into curved panels exhibiting different surface characteristics, and so on; a spherical container can be divided into sectors, segments, lunes, or intersections of those, each exhibiting one of multiple different surface characteristics; the variations and combinations are virtually endless. The preceding examples are not intended to constitute an exhaustive list; additional suitable shapes and arrangements of the container, its areal segments, and their surface characteristics shall fall within the scope of the present disclosure or appended claims.

Figure 1:
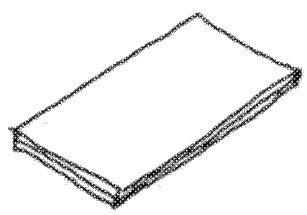
FIG. 1 illustrates schematically a smooth flat surface.
Figure 2:
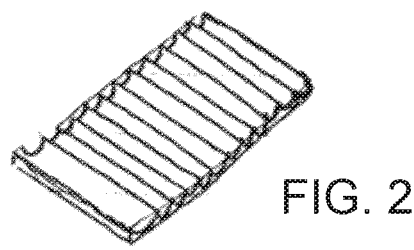
FIG. 2 illustrates schematically a corrugated flat surface.
Figure 3:
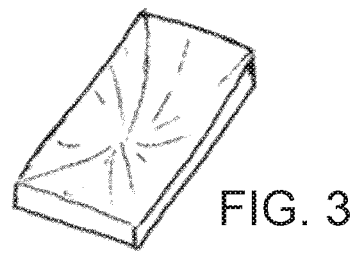
FIG. 3 illustrates schematically a concave surface.
Figure 4:
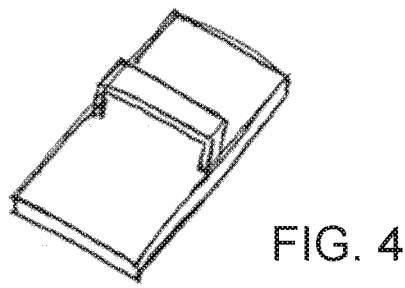
FIG. 4 illustrates schematically a height-discriminating surface.
Figure 5:
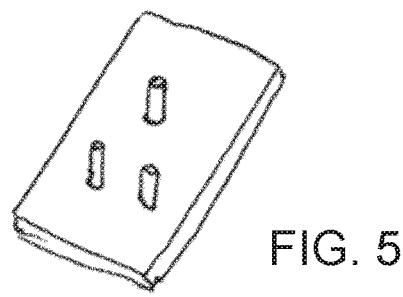
FIG. 5 illustrates schematically a width-discriminating surface.
Figure 14:
FIG. 14 illustrates schematically a concave surface.
Figure 15:
FIG. 15 illustrates schematically a corrugated surface.
Figure 16:
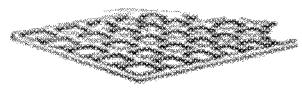
FIG. 16 illustrates schematically a corrugated surface.

The variety of surface characteristics that can be employed also are nearly endless. A given surface characteristic can arise from one or more materials that make up the corresponding areal segment of the container wall, or can arise from a surface layer on or surface treatment of that areal segment, independent of the underlying container wall material. The following examples are not intended to constitute an exhaustive list; additional suitable surface characteristics of the areal segments shall fall within the scope of the present disclosure or appended claims. In various examples, an areal segment can be one or more of: a substantially flat surface (FIGS. 1, 2, 4, 5, 15, and 16); a concave surface (in one or two dimensions; FIGS. 3, 14, and 21); a convex surface (in one or two dimensions); a saddle-shaped surface (i.e., convex on one dimension and concave in the other); a grooved, ribbed, or corrugated surface (including straight, parallel, crossing, lattice-like, curved, spiral, convex, concave, or other arrangements of the ribs, groves, or corrugations; FIGS. 2, 7, 13, 15, and 16); a knobbed, pebbled, or dimpled surface (arranged in a regular pattern or irregularly); a knurled surface; a scalloped surface (FIG. 13), or an undulating surface. In various examples, an areal segment can be one or more of a substantially rigid surface, a hard surface, an elastically deformable surface, a plastically or elastically deformable surface (a deformable areal segment of the container wall, e.g., like a balloon, as in FIG. 19, or a deformable surface layer on an otherwise rigid areal segment of the container wall), a metallic surface, a wooden surface, a paper or cardboard surface, a polymeric or elastomeric surface (e.g., a natural or synthetic solid polymer resin), or a composite surface (e.g., natural or synthetic fibers embedded in a solid polymer matrix). In various examples, an areal segment can be one or more of a roughened or abrasive surface (FIG. 21), a smooth surface (FIGS. 1, 3, 14, and 21), a tacky or sticky surface, a hook or loop surface of a hook-and-loop material (e.g., Velcro®), or a magnetic or electrostatic surface.

Figure 6:
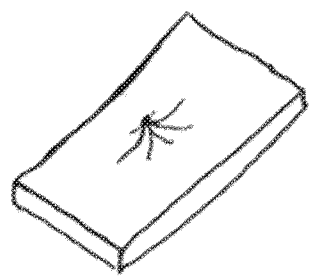
FIG. 6 illustrates schematically a hole-detecting surface.
Figure 20:
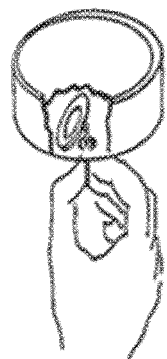
FIG. 20 illustrates schematically sensory input received by inserting a mechanical probe through a hole in a container.
Figure 23:
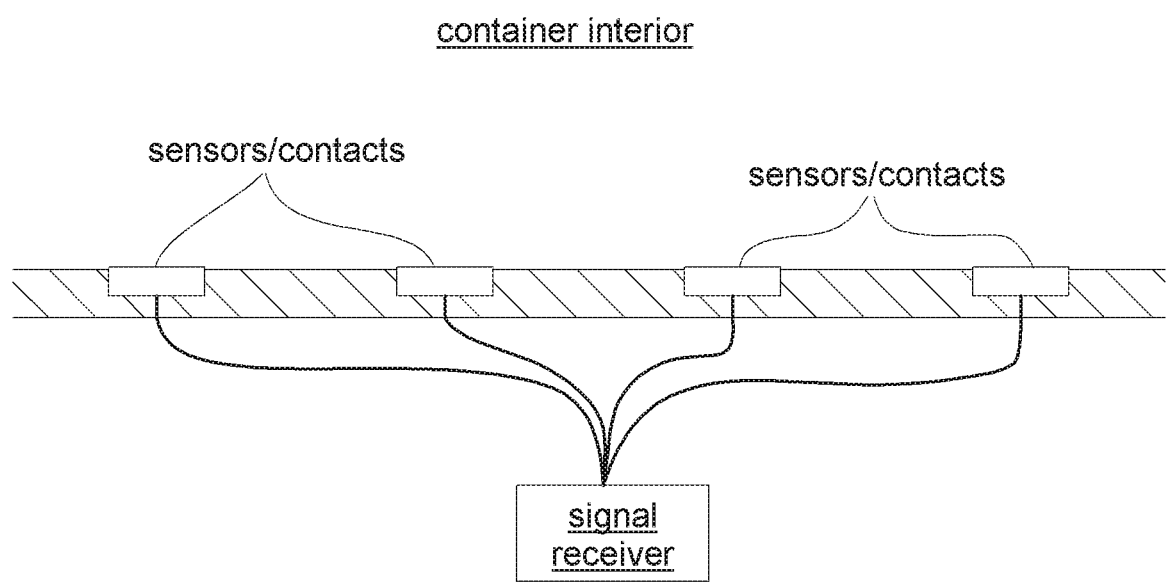
FIG. 23 is a schematic cross sections of an areal segment of a container having one or more electrically connected probe or contact areas.

In various examples, some more complex arrangements can be employed, such as: a height-discriminating surface, e.g., including a low, wide passage that permits objects up to only a certain thickness (adjustable, if needed or desired) to pass beneath it (FIG. 4); a width-discriminating surface, e.g., including multiple posts or pegs spaced so as to permit passage of objects only up to a certain width (FIG. 5; adjustable, if needed or desired); a hole-detecting surface, e.g., including one or more peaks on which a washer or other object with a hole (through or blind) or other depression can be caught and retained (FIGS. 6 and 21); or a set of open-ended slots or chambers arranged like parking slots, uniformly sized and oriented or having various sizes or orientations. In some examples, an areal segment can include a hole through which a user can insert a mechanical probe to feel or manipulate the object within the container (FIG. 20). In some examples (FIG. 23), one or more electrical connected probe or contact areas can be provided on an areal segment; contact between the object and one or more of the areas can be detected or characterized using signals transmitted through electrical conductors through the container wall. Examples of probe or contact areas can include, but are not limited to, simple contacts for determining conductivity of the object, an electrostatic probe, a piezoelectric probe, a temperature probe, or other sensor or probe.

In certain examples, the surface characteristic of at least one of the areal segments is interchangeable with a different surface characteristic. For example, interchangeable panels of differing surface characteristics can be swapped into a six-sided box to provide differing arrangements of surface characteristics. In another example, different inserts or lids can be swapped into or onto a drinking cup.

Typically the container will be filled with air or other gaseous medium; in some examples the container can be partly or completely filled with water or other liquid medium. If there is a liquid medium in the container, its density or viscosity can be chosen to yield desired sensory inputs to the user as the object(s) move through it. In some examples the container can be permanently sealed (i.e., permanent in the sense that opening the container would require damaging or destroying it); in other examples the container can be resealable, e.g., to enable the user to observe the object enclosed within, to enable replacement of the object with a different object, or to enable alteration of one or more of the areal segments of the interior surface. The container can be sealed (permanently or resealably) in any manner suitable for its materials or construction, e.g., glue or other adhesive, tape, string or other tie or ligature, heat or acoustic welding, fasteners of any suitable type, number, and arrangement, a latch or other closure mechanism, and so on.

Just as with the shape of the container and the arrangement and type of surface characteristics of the areal segments of the container's interior surface, the object can also exhibit a wide variety of shapes and characteristics. The following examples are not intended to constitute an exhaustive list; additional suitable shapes and characteristics of the object shall fall within the scope of the present disclosure or appended claims. The (often) solid object can be shaped in any one of myriad three-dimensional shapes, including but not limited to being shaped as a sphere, spheroid, ellipsoid, or ovoid, as a circular or elliptical or oval cylinder or disk, as a circular or elliptical or oval annulus, as a torus or toroid or toroidal polyhedron, as a cube or cuboid, as a rhombohedron or parallelepiped, as a polygonal prism, as a circular or elliptical cone or frustum, as a polygonal pyramid or frustum, as a helix or spiral, as a helical or spiral polyhedron, or as a polyhedron. Common shapes for the object include spherical (e.g., a marble, bead, or ball; FIG. 21), cylindrical (e.g., a pencil), disk-shaped (e.g., a coin), or annular (e.g., a flat washer). The object can be one or more of substantially rigid, elastically deformable, plastically deformable, homogenously dense, heterogeneously dense, solid, hollow, metallic, wooden, paper or cardboard, polymeric, composite, magnetic, smooth, rough or abrasive, tacky or sticky, partly or completely covered with a hook or loop surface of a hook-and-loop material, or electrostatic or magnetic. In some examples, the object can be liquid or semiliquid, foam, or can undergo a phase transition (e.g., a melting ice cube).

Movement of the object while in contact with each one of the multiple areal segments produces a corresponding sensory input to a user holding and moving the container (and thereby causing movement of the object enclosed within the container). Such movements of the object while in contact with an areal segment can include but is not limited to impact with the interior surface, with or without recoil or bouncing, or rolling, sliding, or tumbling across a portion of the areal segment. The differing surface characteristics result in differing corresponding sensory inputs to the user. For example, a glass marble rolling across a hard, dimpled metal surface feels and sounds different (i.e., results in differing tactile and auditory sensory inputs) than a wooden pencil rolling across a corrugated, soft plastic surface, and both of those feel and sound different than a metal coin sliding across a hard, flat, abrasive surface. In many examples, if not most, the differing sensory inputs arising from movement of the object against differing areal segments are tactile and auditory sensory inputs, i.e., feel and sound. In some examples, differing sensory inputs can also include visual or olfactory inputs, possibly enabled or released by contact between the object and a corresponding one of the areal segments. If more than one object in enclosed within the container, interactions between each object and the container interior surfaces, and well as interactions between the objects, can produce sensory inputs to the user. If the container is completely or partially filled with a liquid medium, the relative densities of the object(s) and liquid can be selected to yield desired sensory inputs based on buoyancy or lack thereof, or object hydrodynamic profile(s) can be selected to yield desired sensory inputs desired based on viscous drag.

Figure 17:
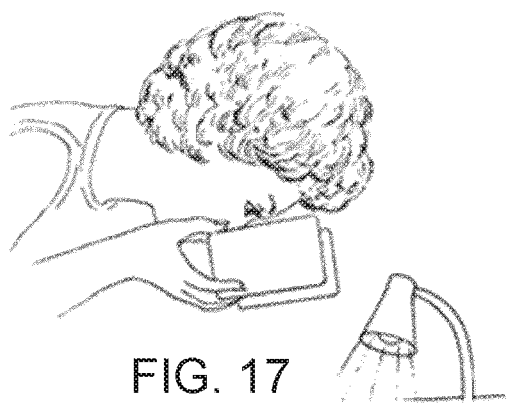
FIG. 17 illustrates schematically a visual sensory input received through a peephole in a container.
Figure 18:
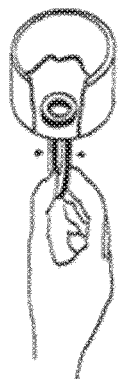
FIG. 18 illustrates schematically sensory input received using a magnet outside a container.
Figure 19:
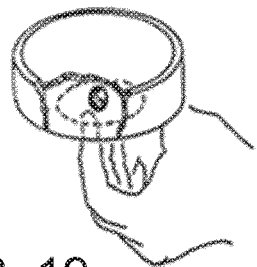
FIG. 19 illustrates schematically sensory input received through a flexible container surface.

In some examples the container is substantially opaque, which would substantially preclude differing visual inputs arising from movement of the object within the container; in other examples, at least a portion of one or more areal segments is transparent or translucent (with or without optical filtering, lensing, or other optical distortion), enabling visual sensory input to the user (e.g., as in FIG. 17, showing a user looking into the container through a peephole). In some examples wherein the object is magnetic, the user can use a magnet moving across the exterior of the box to manipulate the object inside the box to generate additional sensory inputs (FIG. 18). In some examples wherein at least a portion of an areal segment is sufficiently flexible, the user can feel or manipulate the object through the container wall (FIG. 19). In some examples wherein an areal segment includes one or more holes, the user can insert a mechanical probe through the hole to manipulate the object (FIG. 20). In some examples (FIG. 23), one or more electrical connected probe or contact areas can be provided on an areal segment; contact between the object and one or more of the areas can be detected or characterized using signals transmitted through electrical conductors through the container wall and conveyed via one or more sensor readouts. Examples of probe or contact areas can include, but are not limited to, simple contacts for determining conductivity of the object, an electrostatic probe, a piezoelectric probe, a temperature probe, or other sensor or probe.

A method, perhaps performed by an educator, trainer, or therapist, employing the container and object enclosed within it, begins with giving the container to the user with the object enclosed within the container. The user is then asked to (i) identify the object without opening the container (e.g., marble, washer, coin, pencil, etc.), or (ii) infer or deduce characteristics of the object or container without opening the container (e.g., metal, plastic, or wood; convex or concave surface; spherical or cylindrical or polyhedral object; and so on). The user typically will move the container about, often by shaking, tilting, or rotating it, and note the different sounds made and the different feel (e.g., weight, impact, vibration) as the object moves against different areal segments inside the container. The identification, inference, or deduction by the user is based at least in part on the sensory inputs perceived by the user while holding and moving the container with the object enclosed within it. Conversely, a corresponding method performed by the user includes receiving the container with the object contained enclosed within the container, and, without opening the container, identifying the object or inferring or deducing characteristics of the object or container. The user can be given partial information before attempting the identification or characterization, e.g., the user can be given either (i) the identity or one or more characteristics of the object, or (ii) one or more surface characteristics of one or more of the areal segments. The methods can be repeated with a different object enclosed within the same container, the same object enclosed within a different container, or with a different object enclosed within a different container.

The user's identification of the object, or characterization of the object or container, can be evaluated or quantified, by an educator, trainer, or therapist or other user, or by the user him/herself. The evaluation or quantification can be based on any suitable one or more factors, including but not limited to accuracy or time taken. The evaluation or quantification can be employed for entertainment or amusement purposes, e.g., for keeping score in a game (single-player or multi-player, depending on the number of users. Alternatively, the evaluation or quantification can be employed to monitor a user's progress through a regimen of education, training, treatment, or therapy.

The user can employ a score sheet or test matrix or similar device to guide his/her attempted identification or characterization, e.g., on a sheet of paper, on an electronic display (smartphone, computer, tablet, etc.), or even on the container itself; an example is shown in FIG. 22. Such a guide can lead the user through a sequence of manipulations and observations leading to the desired identification or evaluation. The guide can include the correct identification or characterization (e.g., an answer key) so as to enable the user to evaluate his/her identification or characterization, or can include indicators for when a wrong answer or guess is made without revealing the correct answer. Such a key typically would be provided in a form not readily observed by the user, e.g., on a reverse side of a paper sheet, printed upside-down at the bottom of a paper sheet or computer screen, displayed on an electronic screen only in response to a specific command or input (e.g., by reading with a smartphone camera a coded label on the container, or by clicking a link on an electronically displayed guide), printed with a scratch-off coating on a sheet of paper or on the container, and so on.

Instead of a container and object, the methods disclosed above can be simulated using a computing device. A suitable computing device includes one or more digital storage media, one or more digital processors, one or more spatial sensors, and one or more sensory output mechanisms. First, using the one or more spatial sensors, a time sequence of positions, orientations, or movements of the portable computing device is sensed while it is held and moved by the user. Using the one or more processors, and based on the sensed time sequence and a set of simulation parameters stored in the one or more storage media, a time sequence of corresponding sensory outputs is computed. Using the one or more sensory output mechanisms, and based on the computed time sequence, the sensory outputs of the computed time sequence are produced so as to be perceived as corresponding sensory inputs by the user holding and moving the portable computing device. The user thus perceives the same sensory output (e.g., sound and feel) that he/she would perceive if holding and moving the container with the object enclosed within it. Simulation parameters for any desired number and type of different object/container combinations can be stored by the computing device. A set of parameters can be selected at random or selected by an educator, trainer, therapist, or fellow user, or can be indicated by a provided code read into the computing device (e.g., an alphanumeric code typed into the computing device or a barcode, QR code, or other spatial code read by a camera or other optical sensor of the computing device; such codes can be printed on the corresponding container, or can be printed on a sheet of paper or rendered on an electronic display without any corresponding container present or even existing).

The one or more spatial sensors can include one or more accelerometers, one or more position sensors, or one or more orientation sensors. The one or more sensory output mechanisms includes one or more vibratory mechanisms or one or more audio speakers, and can also include one or more visual displays or one or more olfactory sources. The portable computing device can comprises a smartphone, a gaming controller, a tablet, a handheld computer, a notebook computer, or a laptop computer.

In addition to the preceding, the following examples fall within the scope of the present disclosure or appended claims:

Example 1

An article comprising a container and one or more objects enclosed within the container, wherein: (a) an interior volume of the container is at least partly bounded by an interior surface of the container that comprises two or more distinct areal segments, and each one of the areal segments exhibits a corresponding surface characteristic; (b) the container and the object are structurally arranged so that (i) the one or more objects are at least partly constrained to remain within the interior volume of the container, (ii) the one or more objects are movable within the interior volume of the container, and (iii) movement of each one of the one or more objects while in contact with each one of the areal segments results in a corresponding sensory input to a user moving the container; and (c) the corresponding surface characteristic of each one of the areal segments differs from the corresponding surface characteristic of at least one other of the areal segments, so that the corresponding sensory input to the user resulting from movement of a given one of the one or more objects while in contact with that areal segment differs from the corresponding sensory input resulting from movement of the given object while in contact with at least one other of the areal segments.

Example 2

The article of Example 1 wherein at least one of the one or more objects is a solid object.

Example 3

The article of any one of Examples 1 or 2 wherein only a single object is enclosed within the container.

Example 4

The article of any one of Examples 1 through 3 wherein the interior volume of the container is entirely bounded by the interior surface of the container so that the one or more objects are constrained to remain within the interior volume of the container.

Example 5

The article of any one of Examples 1 through 4 wherein the surface characteristic of at least one of the areal segments includes one or more of a substantially flat surface, a concave surface, a convex surface, a corrugated surface, a knobbed or pebbled or dimpled surface, a knurled surface, a scalloped surface, or an undulating surface.

Example 6

The article of any one of Examples 1 through 5 wherein the surface characteristic of at least one of the areal segments includes one or more of a height-discriminating surface, a width-discriminating surface, or a hole-detecting surface.

Example 7

The article of any one of Examples 1 through 6 wherein the surface characteristic of at least one of the areal segments includes one or more of a substantially rigid surface, a hard surface, an elastically deformable surface, a plastically deformable surface, a metallic surface, a wooden surface, a paper or cardboard surface, a polymeric surface, an elastomeric surface, or a composite surface.

Example 8

The article of any one of Examples 1 through 7 wherein the surface characteristic of at least one of the areal segments includes one or more of a roughened or abrasive surface, a smooth surface, a tacky or sticky surface, a hook or loop surface of a hook-and-loop material, or a magnetic or electrostatic surface.

Example 9

The article of any one of Examples 1 through 8 wherein the surface characteristic of at least one of the areal segments is interchangeable with a different surface characteristic.

Example 10

The article of any one of Examples 1 through 9 wherein the surface characteristic of at least one of the areal segments includes one or more holes structurally arranged for receiving therethrough a mechanical probe.

Example 11

The article of any one of Examples 1 through 10 wherein the surface characteristic of at least one of the areal segments includes one or more electrically connected contact or sensor areas.

Example 12

The article of any one of Examples 1 through 11 wherein the container is shaped as a sphere, spheroid, ellipsoid, ovoid, circular or elliptical or oval cylinder or disk, circular or elliptical or oval annulus, torus or toroid or toroidal polyhedron, cube or cuboid, rhombohedron or parallelepiped, polygonal prism, circular or elliptical cone or frustum, polygonal pyramid or frustum, or polyhedron.

Example 13

The article of any one of Examples 1 through 12 wherein at least one of the one or more objects is shaped as a sphere, spheroid, ellipsoid, ovoid, circular or elliptical or oval cylinder or disk, circular or elliptical or oval annulus, torus or toroid or toroidal polyhedron, cube or cuboid, rhombohedron or parallelepiped, polygonal prism, circular or elliptical cone or frustum, polygonal pyramid or frustum, helix or spiral, helical or spiral polyhedron, or polyhedron.

Example 14

The article of any one of Examples 1 through 13 wherein at least one of the one or more objects is one or more of substantially rigid, elastically deformable, plastically deformable, homogenously dense, heterogeneously dense, solid, hollow, metallic, wooden, paper or cardboard, polymeric, elastomeric, composite, magnetic, smooth, rough or abrasive, tacky or sticky or possessed of a hook or loop surface of a hook-and-lop material, or magnetic or electrostatic.

Example 15

The article of any one of Examples 1 through 14 wherein one or more of the objects are liquid or semiliquid or foam.

Example 16

The article of any one of Examples 1 through 15 wherein the corresponding sensory inputs include auditory inputs or tactile inputs.

Example 17

The article of any one of Examples 1 through 16 wherein the corresponding sensory inputs include visual inputs or olfactory inputs or sensor readouts.

Example 18

The article of any one of Examples 1 through 17 wherein the container is substantially opaque.

Example 19

The article of any one of Examples 1 through 17 wherein at least a portion of one or more of the areal segments is translucent or transparent.

Example 20

A method performed using the article of any one of Examples 1 through 19, the method comprising: (A) giving the container with the one or more objects enclosed within the container to the user; and (B) after part (A), instructing the user to (i) identify one or more of the objects without opening the container, or (ii) infer or deduce characteristics of one or more of the areal segments or one or more of the objects without opening the container, (C) wherein the identification, inference, or deduction is based at least in part on sensory inputs perceived by the user while moving the container with the one or more objects enclosed within the container.

Example 21

The method of Example 20 further comprising evaluating or quantifying the user's identification of one or more of the objects or characterization of one or more of the objects or areal segments.

Example 22

The method of any one of Examples 20 or 21 further comprising repeating parts (A) and (B) with (i) the same one or more objects enclosed within in a different container, (ii) a different or additional one or more objects enclosed within the same container, or (iii) a different or additional one or more objects enclosed within a different container.

Example 23

The method of any one of Examples 20 through 22 further comprising, after part (A), identifying one or more of the objects to the user, and instructing the user to infer or deduce characteristics of one or more of the areal segments without opening the container.

Example 24

The method of any one of Examples 20 through 22 wherein further comprising, after part (A), identifying one or more of the corresponding surface characteristics to the user, and instructing the user to (i) identify one or more of the objects without opening the container, or (ii) infer or deduce characteristics of one or more of the objects without opening the container.

Example 25

A method performed by the user employing the article of any one of Examples 1 through 19, the method comprising: (A) receiving the container with the one or more objects contained enclosed within the container; and (B) after part (A), without opening the container, identifying one or more of the objects or inferring or deducing characteristics of one or more of the areal segments or one or more of the objects, (C) wherein the identification, inference, or deduction is based at least in part on sensory inputs perceived by the user while moving the container with the one or more objects enclosed within the container.

Example 26

The method of Example 25 further comprising evaluating or quantifying the user's own identification of one or more of the objects or characterization of one or more of the objects or areal segments.

Example 27

The method of any one of Examples 25 or 26 further comprising repeating parts (A) and (B) with (i) the same one or more objects enclosed within in a different container, (ii) a different or additional one or more objects enclosed within the same container, or (iii) a different or additional one or more objects enclosed within a different container.

Example 28

The method of any one of Examples 25 through 27 further comprising, after part (A), receiving information identifying one or more of the objects, and inferring or deducing characteristics of one or more of the areal segments without opening the container.

Example 29

The method of any one of Examples 25 through 27 further comprising, after part (A), receiving information identifying one or more of the corresponding surface characteristics, and, without opening the container, identifying one or more of the objects or inferring or deducing characteristics of one or more of the objects without opening the container.

Example 30

A method for providing sensory input to a user using a portable computing device that includes one or more digital storage media, one or more digital processors, one or more spatial sensors, and one or more sensory output mechanisms, the method comprising: (a) using the one or more spatial sensors, sensing a time sequence of positions, orientations, or movements of the portable computing device moved by the user; (b) using the one or more processors, based on (i) the sensed time sequence and (ii) a set of simulation parameters stored in the one or more storage media, computing a time sequence of corresponding sensory outputs; and (c) using the one or more sensory output mechanisms, based on the computed time sequence, producing the sensory outputs of the computed time sequence so as to be perceived as corresponding sensory inputs by the user holding and moving the portable computing device, (d) wherein the computed time sequence simulates sensory inputs that would be perceived by the user if the user were holding a container with one or more objects enclosed within the container, and (1) an interior volume of the container were bounded by an interior surface of the container that comprises two or more distinct areal segments, and each one of the areal segments were to exhibit a corresponding surface characteristic; (2) the container and the one or more objects were structurally arranged so that (i) the one or more objects are constrained to remain within the interior volume of the container, (ii) the one or more objects are movable within the interior volume of the container, and (iii) movement of each one of the one or more objects while in contact with each one of the areal segments results in a corresponding sensory input to a user moving the container; and (3) the corresponding surface characteristic of each one of the areal segments were to differ from the corresponding surface characteristic of at least one other of the areal segments, so that the corresponding sensory input to the user resulting from movement of a given one of the one or more objects while in contact with that areal segment differs from the corresponding sensory input resulting from movement of the given object while in contact with at least one other of the areal segments.

Example 31

The method of Example 30 wherein the one or more spatial sensors include one or more accelerometers, one or more position sensors, or one or more orientation sensors.

Example 32

The method of any one of Examples 30 or 31 wherein the one or more sensory output mechanisms includes one or more vibratory mechanisms or one or more audio speakers.

Example 33

The method of any one of Examples 30 through 32 wherein the one or more sensory output mechanisms includes one or more visual displays or one or more olfactory sources or one or more sensor readouts.

Example 34

The method of any one of Examples 30 through 33 wherein the portable computing device comprises a smartphone, a gaming controller, a tablet, a handheld computer, a notebook computer, or a laptop computer.

Example 35

The method of any one or Examples 20 through 29 performed with a portable computing device in place of the article of any one of examples 1 through 19, using the method of any one of Examples 30 through 34, wherein the portable computing device is structured and programmed to simulate the article of any one of Examples 1 through 19.

It is intended that equivalents of the disclosed example embodiments and methods shall fall within the scope of the present disclosure or appended claims. It is intended that the disclosed example embodiments and methods, and equivalents thereof, may be modified while remaining within the scope of the present disclosure or appended claims.

In the foregoing Detailed Description, various features may be grouped together in several example embodiments for the purpose of streamlining the disclosure. This method of disclosure is not to be interpreted as reflecting an intention that any claimed embodiment requires more features than are expressly recited in the corresponding claim. Rather, as the appended claims reflect, inventive subject matter may lie in less than all features of a single disclosed example embodiment. Thus, the appended claims are hereby incorporated into the Detailed Description, with each claim standing on its own as a separate disclosed embodiment. However, the present disclosure shall also be construed as implicitly disclosing any embodiment having any suitable set of one or more disclosed or claimed features (i.e., a set of features that are neither incompatible nor mutually exclusive) that appear in the present disclosure or the appended claims, including those sets that may not be explicitly disclosed herein. In addition, for purposes of disclosure, each of the appended dependent claims shall be construed as if written in multiple dependent form and dependent upon all preceding claims with which it is not inconsistent. It should be further noted that the scope of the appended claims does not necessarily encompass the whole of the subject matter disclosed herein.

For purposes of the present disclosure and appended claims, the conjunction "or" is to be construed inclusively (e.g., "a dog or a cat" would be interpreted as "a dog, or a cat, or both"; e.g., "a dog, a cat, or a mouse" would be interpreted as "a dog, or a cat, or a mouse, or any two, or all three"), unless: (i) it is explicitly stated otherwise, e.g., by use of "either . . . or," "only one of," or similar language; or (ii) two or more of the listed alternatives are mutually exclusive within the particular context, in which case "or" would encompass only those combinations involving non-mutually-exclusive alternatives. For purposes of the present disclosure and appended claims, the words "comprising," "including," "having," and variants thereof, wherever they appear, shall be construed as open ended terminology, with the same meaning as if the phrase "at least" were appended after each instance thereof, unless explicitly stated otherwise. For purposes of the present disclosure or appended claims, when terms are employed such as "about equal to," "substantially equal to," "greater than about," "less than about," and so forth, in relation to a numerical quantity, standard conventions pertaining to measurement precision and significant digits shall apply, unless a differing interpretation is explicitly set forth. For null quantities described by phrases such as "substantially prevented," "substantially absent," "substantially eliminated," "about equal to zero," "negligible," and so forth, each such phrase shall denote the case wherein the quantity in question has been reduced or diminished to such an extent that, for practical purposes in the context of the intended operation or use of the disclosed or claimed apparatus or method, the overall behavior or performance of the apparatus or method does not differ from that which would have occurred had the null quantity in fact been completely removed, exactly equal to zero, or otherwise exactly nulled.

In the appended claims, any labelling of elements, steps, limitations, or other portions of a claim (e.g., (a), (b), (c), etc., or (i), (ii), (iii), etc.) is only for purposes of clarity, and shall not be construed as implying any sort of ordering or precedence of the claim portions so labelled. If any such ordering or precedence is intended, it will be explicitly recited in the claim. In the appended claims, if the provisions of 35 USC § 112(f) are desired to be invoked in an apparatus claim, then the word "means" will appear in that apparatus claim. If those provisions are desired to be invoked in a method claim, the words "a step for" will appear in that method claim. Conversely, if the words "means" or "a step for" do not appear in a claim, then the provisions of 35 USC § 112(f) are not intended to be invoked for that claim.

If any one or more disclosures are incorporated herein by reference and such incorporated disclosures conflict in part or whole with, or differ in scope from, the present disclosure, then to the extent of conflict, broader disclosure, or broader definition of terms, the present disclosure controls. If such incorporated disclosures conflict in part or whole with one another, then to the extent of conflict, the later-dated disclosure controls.

The Abstract is provided as required as an aid to those searching for specific subject matter within the patent literature. However, the Abstract is not intended to imply that any elements, features, or limitations recited therein are necessarily encompassed by any particular claim. The scope of subject matter encompassed by each claim shall be determined by the recitation of only that claim.

What is claimed is:

1. An article comprising a container and one or more objects enclosed within the container, wherein:
   (a) an interior volume of the container is at least partly bounded by an interior surface of the container that comprises two or more distinct areal segments, and each one of the areal segments exhibits a corresponding surface characteristic;
   (b) the container and the object are structurally arranged so that (i) the one or more objects are at least partly constrained to remain within the interior volume of the container, (ii) the one or more objects are movable within the interior volume of the container, and (iii)

movement of each one of the one or more objects while in contact with each one of the areal segments results in a corresponding sensory input to a user moving the container; and (c) the corresponding surface characteristic of each one of the areal segments differs from the corresponding surface characteristic of at least one other of the areal segments, so that the corresponding sensory input to the user resulting from movement of a given one of the one or more objects while in contact with that areal segment differs from the corresponding sensory input resulting from movement of the given object while in contact with at least one other of the areal segments.

2. The article of claim 1 wherein at least one of the one or more objects is a solid object.

3. The article of claim 1 wherein only a single object is enclosed within the container.

4. The article of claim 1 wherein the interior volume of the container is entirely bounded by the interior surface of the container so that the one or more objects are constrained to remain within the interior volume of the container.

5. The article of claim 1 wherein the surface characteristic of at least one of the areal segments includes one or more of a substantially flat surface, a concave surface, a convex surface, a corrugated surface, a knobbed or pebbled or dimpled surface, a knurled surface, a scalloped surface, or an undulating surface.

6. The article of claim 1 wherein the surface characteristic of at least one of the areal segments includes one or more of a height-discriminating surface, a width-discriminating surface, or a hole-detecting surface.

7. The article of claim 1 wherein the surface characteristic of at least one of the areal segments includes one or more of a substantially rigid surface, a hard surface, an elastically deformable surface, a plastically deformable surface, a metallic surface, a wooden surface, a paper or cardboard surface, a polymeric surface, an elastomeric surface, or a composite surface.

8. The article of claim 1 wherein the surface characteristic of at least one of the areal segments includes one or more of a roughened or abrasive surface, a smooth surface, a tacky or sticky surface, a hook or loop surface of a hook-and-loop material, or a magnetic or electrostatic surface.

9. The article of claim 1 wherein the surface characteristic of at least one of the areal segments is interchangeable with a different surface characteristic.

10. The article of claim 1 wherein the surface characteristic of at least one of the areal segments includes one or more holes structurally arranged for receiving therethrough a mechanical probe.

11. The article of claim 1 wherein the surface characteristic of at least one of the areal segments includes one or more electrically connected contact or sensor areas.

12. The article of claim 1 wherein the container is shaped as a sphere, spheroid, ellipsoid, ovoid, circular or elliptical or oval cylinder or disk, circular or elliptical or oval annulus, torus or toroid or toroidal polyhedron, cube or cuboid, rhombohedron or parallelepiped, polygonal prism, circular or elliptical cone or frustum, polygonal pyramid or frustum, or polyhedron.

13. The article of claim 1 wherein at least one of the one or more objects is shaped as a sphere, spheroid, ellipsoid, ovoid, circular or elliptical or oval cylinder or disk, circular or elliptical or oval annulus, torus or toroid or toroidal polyhedron, cube or cuboid, rhombohedron or parallelepiped, polygonal prism, circular or elliptical cone or frustum, polygonal pyramid or frustum, helix or spiral, helical or spiral polyhedron, or polyhedron.

14. The article of claim 1 wherein at least one of the one or more objects is one or more of substantially rigid, elastically deformable, plastically deformable, homogenously dense, heterogeneously dense, solid, hollow, metallic, wooden, paper or cardboard, polymeric, elastomeric, composite, magnetic, smooth, rough or abrasive, tacky or sticky, a hook or loop surface of a hook-and-lop material, or magnetic or electrostatic.

15. The article of claim 1 wherein at least one of the one or more objects is liquid or semiliquid or foam.

16. The article of claim 1 wherein the container is substantially opaque.

17. The article of claim 1 wherein the corresponding sensory inputs include auditory inputs or tactile inputs.

18. The article of claim 1 wherein the corresponding sensory inputs include visual inputs or olfactory inputs or sensor readouts.

19. The article of claim 1 wherein at least a portion of one or more of the areal segments is translucent or transparent.

20. A method performed by the user employing the article of claim 1, the method comprising:

(A) receiving the container with the one or more objects enclosed within the container;

(B) after part (A), moving the container by one or more of shaking, tilting, or rotating the container and observing sensory inputs arising from movement of the container, including one or more of sounds, tactile sensations, weight, impact, or vibration; and (C) without opening the container, identifying, based on the observed sensory inputs, one or more of the objects or inferring or deducing, based on the observed sensory inputs, characteristics of one or more of the areal segments or one or more of the objects.

21. The method of claim 20 further comprising evaluating or quantifying the user's own identification of one or more of the objects or characterization of one or more of the objects or areal segments.

22. The method of claim 20 further comprising repeating parts (A) through (C) with (i) the same one or more objects enclosed within in a different container, (ii) a different or additional one or more objects enclosed within the same container, or (iii) a different or additional one or more objects enclosed within a different container.

23. The method of claim 20 further comprising receiving information identifying one or more of the objects, and inferring or deducing characteristics of one or more of the areal segments without opening the container.

24. The method of claim 20 further comprising receiving information identifying one or more of the corresponding surface characteristics, and, without opening the container, identifying one or more of the objects or inferring or deducing characteristics of one or more of the objects without opening the container.

* * * * *